United States Patent
Oliver et al.

(10) Patent No.: US 11,884,737 B2
(45) Date of Patent: Jan. 30, 2024

(54) TREATMENT OF AUTOIMMUNE DISORDERS WITH CD154 ANTIBODIES

(71) Applicants: UCB BIOPHARMA SRL, Brussels (BE); BIOGEN MA INC., Cambridge, MA (US)

(72) Inventors: Ruth Oliver, Slough (GB); Miren Zamacona, Slough (GB)

(73) Assignees: UCB BIOPHARMA SRL, Brussels (BE); BIOGEN MA INC., Cambridge, MA (US)

( * ) Notice: Subject to any disclaimer, the term of this patent is extended or adjusted under 35 U.S.C. 154(b) by 0 days.

(21) Appl. No.: 17/361,393

(22) Filed: Jun. 29, 2021

(65) Prior Publication Data

US 2021/0324095 A1 Oct. 21, 2021

Related U.S. Application Data

(63) Continuation of application No. 15/547,223, filed as application No. PCT/EP2015/059095 on Apr. 27, 2015, now abandoned.

(30) Foreign Application Priority Data

Jan. 30, 2015 (GB) .................................. 1501613

(51) Int. Cl.
*C07K 16/02* (2006.01)
*A61K 39/395* (2006.01)
*A61P 37/06* (2006.01)
*C07K 16/28* (2006.01)
*A61K 39/00* (2006.01)

(52) U.S. Cl.
CPC ........ *C07K 16/2875* (2013.01); *A61K 39/395* (2013.01); *A61K 2039/505* (2013.01); *A61K 2039/545* (2013.01); *C07K 2317/35* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,293,237 B2 | 10/2012 | Burkly et al. |
| 8,784,823 B2 | 7/2014 | Burkly et al. |
| 9,321,840 B2 | 4/2016 | Burkly et al. |
| 2010/0104573 A1 | 4/2010 | Burkly et al. |
| 2012/0121585 A1 | 5/2012 | Heusser et al. |
| 2014/0056889 A1 | 2/2014 | Morimoto et al. |
| 2016/0200823 A1 | 7/2016 | Burkly et al. |

FOREIGN PATENT DOCUMENTS

| | | |
|---|---|---|
| WO | WO 02/18445 | 3/2002 |
| WO | WO 2008/118356 | 10/2008 |
| WO | WO 2010/065819 | 6/2010 |

OTHER PUBLICATIONS

NCT01764594 (as updated on Aug. 26, 2014); 3 pages.*
Boumpas, D. T. et al. "A Short Course of BG9588 (Anti-CD40 Ligand Antibody) Improves Serologic Activity and Decreases Hematuria in Patients With Proliferative Lupus Glomerulonephritis" *Arthritis & Rheumatism*, Mar. 2003, pp. 719-727, vol. 48, No. 3.
Anonymous, "Safety Study of CDP7657 in Healthy Volunteers and Patients With Systematic Lupus Erythematosus (SLE)" Jan. 3, 2013, retrieved from the internet, URL:https://www.clinicaltrials.gov/ct2/show/NCT01093911?term=CDP7657&rank=1, retrieved on Jun. 16, 2015, pp. 1-2.
Anonymous, "Safety Study of CDP7657 in Patients With Systematic Lupus Erythematosus" Aug. 26, 2014, retrieved from the internet, URL:https://www.clinicaltrials.gov/ct2/show/NCT01764594?term=CDP7657&rank=2, retrieved on Jun. 16, 2015, pp. 1-3.
Wakefield, I. et al. "CDP7657, A Monovalent FAB Peg Anti-CD40L Antibody, Inhibits Immune Responses in Both HuSCID Mice and Non-Human Primates" *Arthritis & Rheumatism*, Nov. 2010, Abstract Supplement, p. 1, vol. 62.
Wakefield, I. et al. "CDP7657, A Monovalent FAB' Peg Anti-CD40L Antibody, Inhibits Immune Responses in Both HuSCID Mice and Non-Human Primates" *Ann Rheum Dis*, Jan. 1, 2011, p. 525, vol. 70, Suppl. 3.
Written Opinion in International Application No. PCT/EP2015/059095, dated Jul. 7, 2015, pp. 1-6.
Anonymous, "History of Changes for Study: NCT01764594", study record version 1, Jan. 9, 2013 [estimate], retrieved from the internet, https://clinicaltrials.gov/ct2/history/NCT01764594?V_1=View#StudyPageTop, retrieved on Apr. 2, 2020, pp. 1-4.
Anonymous, "History of Changes for Study: NCT01764594", study record version 2, Jan. 21, 2013 [estimate], retrieved from the internet, https://clinicaltrials.gov/ct2/history/NCT01764594?V_2=View#StudyPageTop, retrieved on Apr. 2, 2020, pp. 1-4.
Anonymous, "History of Changes for Study: NCT01764594", study record version 3, Feb. 28, 2013 [estimate], retrieved from the internet, https://clinicaltrials.gov/ct2/history/NCT01764594?V_3=View#StudyPageTop, retrieved on Apr. 2, 2020, pp. 1-4.
Anonymous, "History of Changes for Study: NCT01764594", study record version 4, Apr. 1, 2013 [estimate], retrieved from the internet, https://clinicaltrials.gov/ct2/history/NCT01764594?V_4=View#StudyPageTop, retrieved on Apr. 2, 2020, pp. 1-4.
Anonymous, "History of Changes for Study: NCT01764594", study record version 5, Apr. 25, 2013 [estimate], retrieved from the internet, https://clinicaltrials.gov/ct2/history/NCT01764594?V_5=View#StudyPageTop, retrieved on Apr. 2, 2020, pp. 1-4.
Anonymous, "History of Changes for Study: NCT01764594", study record version 6, May 30, 2013 [estimate], retrieved from the internet, https://clinicaltrials.gov/ct2/history/NCT01764594?V_6=View#StudyPageTop, retrieved on Apr. 2, 2020, pp. 1-4.

(Continued)

*Primary Examiner* — Ilia I Ouspenski
(74) *Attorney, Agent, or Firm* — SALIWANCHIK, LLOYD & EISENSCHENK

(57) ABSTRACT

The present invention relates to a method of treating an autoimmune or inflammatory disease or a neurodegenerative disease with an antibody to CD154.

11 Claims, 8 Drawing Sheets

Specification includes a Sequence Listing.

(56) References Cited

OTHER PUBLICATIONS

Anonymous, "History of Changes for Study: NCT01764594", study record version 7, May 31, 2013 [estimate], retrieved from the internet, https://clinicaltrials.gov/ct2/history/NCT01764594?V_7=View#StudyPageTop, retrieved on Apr. 2, 2020, pp. 1-4.
Anonymous, "History of Changes for Study: NCT01764594", study record version 8, Jun. 5, 2013 [estimate], retrieved from the internet, https://clinicaltrials.gov/ct2/history/NCT01764594?V_8=View#StudyPageTop, retrieved on Apr. 2, 2020, pp. 1-4.
Anonymous, "History of Changes for Study: NCT01764594", study record version 9, Jun. 27, 2013 [estimate], retrieved from the internet, https://clinicaltrials.gov/ct2/history/NCT01764594?V_9=View#StudyPageTop, retrieved on Apr. 2, 2020, pp. 1-4.
Anonymous, "History of Changes for Study: NCT01764594", study record version 10, Aug. 23, 2013 [estimate], retrieved from the internet, https://clinicaltrials.gov/ct2/history/NCT01764594?V_10=View#StudyPageTop, retrieved on Apr. 2, 2020, pp. 1-5.
Anonymous, "History of Changes for Study: NCT01764594", study record version 11, Oct. 31, 2013 [estimate], retrieved from the internet, https://clinicaltrials.gov/ct2/history/NCT01764594?V_11=View#StudyPageTop, retrieved on Apr. 2, 2020, pp. 1-5.
Anonymous, "History of Changes for Study: NCT01764594", study record version 12, Nov. 1, 2013 [estimate], retrieved from the internet, https://clinicaltrials.gov/ct2/history/NCT01764594?V_12=View#StudyPageTop, retrieved on Apr. 2, 2020, pp. 1-5.
Anonymous, "History of Changes for Study: NCT01764594", study record version 13, Nov. 25, 2013 [estimate], retrieved from the internet, https://clinicaltrials.gov/ct2/history/NCT01764594?V_13=View#StudyPageTop, retrieved on Apr. 2, 2020, pp. 1-5.
Anonymous, "History of Changes for Study: NCT01764594", study record version 14, Jan. 28, 2014 [estimate], retrieved from the internet, https://clinicaltrials.gov/ct2/history/NCT01764594?V_14=View#StudyPageTop, retrieved on Apr. 2, 2020, pp. 1-5.
Anonymous, "History of Changes for Study: NCT01764594", study record version 15, Feb. 21, 2014 [estimate], retrieved from the internet, https://clinicaltrials.gov/ct2/history/NCT01764594?V_15=View#StudyPageTop, retrieved on Apr. 2, 2020, pp. 1-4.
Anonymous, "History of Changes for Study: NCT01764594", study record version 16, Apr. 29, 2014 [estimate], retrieved from the internet, https://clinicaltrials.gov/ct2/history/NCT01764594?V_16=View#StudyPageTop, retrieved on Apr. 2, 2020, pp. 1-4.
Anonymous, "History of Changes for Study: NCT01764594", study record version 17, Apr. 30, 2014 [estimate], retrieved from the internet, https://clinicaltrials.gov/ct2/history/NCT01764594?V_17=View#StudyPageTop, retrieved on Apr. 2, 2020, pp. 1-4.
Anonymous, "History of Changes for Study: NCT01764594", study record version 18, May 1, 2014 [estimate], retrieved from the internet, https://clinicaltrials.gov/ct2/history/NCT01764594?V_18=View#StudyPageTop, retrieved on Apr. 2, 20202, pp. 1-4.
Anonymous, "History of Changes for Study: NCT01764594", study record version 19, Jun. 27, 2014 [estimate], retrieved from the internet, https://clinicaltrials.gov/ct2/history/NCT01764594?V_19=View#StudyPageTop, retrieved on Apr. 2, 2020, pp. 1-4.
Anonymous, "History of Changes for Study: NCT01764594", study record version 20, Aug. 27, 2014 [estimate], retrieved from the internet, https://clinicaltrials.gov/ct2/history/NCT01764594?V_20=View#StudyPageTop, retrieved on Apr. 2, 2020, pp. 1-4.
Anonymous, "History of Changes for Study: NCT01764594", study record version 21, Jul. 16, 2015 [estimate], retrieved from the internet, https://clinicaltrials.gov/ct2/history/NCT01764594?V_21=View#StudyPageTop, retrieved on Apr. 2, 2020, pp. 1-4.
Rudikoff, S. et al. "Single amino acid substitution altering antigen-binding specificity" Proc Natl Acad Sci USA., Mar. 1982, pp. 1979-1983, vol. 79.
Colman, p. M. "Effects of amino acid sequence changes on antibody-antigen interactions" *Research in Immunology*, 1994, pp. 33-36, vol. 145.
Kussie, P. H. et al. "A Single Engineered Amino Acid Substitution Changes Antibody Fine Specificity" *Journal of Immunology*, 1994, pp. 146-152, vol. 152.
Chen, C. et al. "Enhancement and destruction of antibody function by somatic mutation: unequal occurrence is controlled by V gene combinatorial associations" *The EMBO Journal*, 1995, pp. 2784-2794, vol. 14, No. 12.
D'Angelo, S. et al. "Many Routes to an Antibody Heavy-Chain CDR3: Necessary, Yet Insufficient, for Specific Binding" *Frontiers in Immunology*, Mar. 2018, pp. 1-13, vol. 9, Article 395.
Piche-Nicholas, N. M. et al. "Changes in complemetarity-determining regions significantly alter IgG binding to the neonatal Fc receptor (FcRn) and pharmacokinetics" *MABS*, 2018, pp. 81-94, vol. 10, No. 1.
Ruplizumab printout from ChemIDplus, retrieved from https://chem.nlm.nih.gov/chemidplus/name/ruplizumab, Nov. 13, 2020, pp. 1-2.
Dapirolizumab printout from ChemIDplus, retrieved from https://chem.nlm.nih.gov/chemidplus/rn/141614 7-64-2, Nov. 13, 2020, pp. 1-3.
Alturaihi, H. et al. "Interaction of CD154 with different receptors and its role in bidirectional signals" *Eur. J. Immunol.*, 2015, pp. 592-602, vol. 45.
Okimura K. et al. "Characterization of ASKP1240, a Fully Human Antibody Targeting Human CD40 With Potent Immunosuppressive Effects" *American Journal of Transplantation*, 2014, pp. 1290-1299, vol. 74.
Kato, K. et al. "The soluble CD40 ligand sCD154 in systemic lupus erythematosus" *The Journal of Clinical Investigation*, Oct. 1999, pp. 947-955, vol. 104, No. 7.
Touma, Z. et al. "Systemic Lupus Erythematosus Disease Activity Index 2000 Responder Index-50 Enhances the Ability of SLE Responder Index to Identify Responders in Clinical Trials" *The Journal of Rheumatology*, 2011, pp. 2395-2399, vol. 38, No. 11.
Jain, M. et al. "Engineering antibodies for clinical applications" *TRENDS in Biotechnology*, available online May 21, 2007, pp. 307-316, vol. 25, No. 7.
Xenaki, K. T. et al. "Antibody or Antibody Fragments: Implications for Molecular Imaging and Targeted Therapy of Solid Tumors" *Frontiers in Immunology*, Oct. 12, 2017, pp. 1-6, vol. 8, No. 1287.

* cited by examiner

Fig. 1

Assessment of immunogenicity – CD154 antibodies in subjects with SLE

| Dose Group | 5 mg/kg (n=3) | | | 15 mg/kg (n=3) | | | 30 mg/kg (n=4) | | | 60 mg/kg (n=3) | | |
|---|---|---|---|---|---|---|---|---|---|---|---|---|
| Visit | Nobs | Min units/mL | Max | Nobs | Min units/mL | Max | Nobs | Min units/mL | Max | Nobs | Min units/mL | Max |
| Day 7 | 0 | | | 0 | | | 0 | | | | | |
| Day 14 | 0 | | | 0 | | | 0 | | | | | |
| Day 28 | 1 | 0.0090 | 0.0090 | 0 | | | 0 | | | | | |
| Day 42 | 2 | 0.0067 | 0.0227 | 0 | | | 0 | | | | | |
| Day 56 | 3 | 0.0162 | 0.0361 | 1 | 0.0082 | 0.0082 | 0 | | | | | |
| Day 70 | 3 | 0.0247 | 0.0719 | 0 | | | 0 | | | | | |
| Day 84 | 3 | 0.0328 | 0.0887 | 2 | 0.0086 | 0.0103 | 2 | 0.0073 | 0.0095 | 2 | 0.0131 | 0.0236 |
| Day 98 | 3 | 0.0217 | 0.0695 | 2 | 0.0157 | 0.0161 | 3 | 0.0092 | 0.0365 | 3 | 0.0072 | 0.1010 |
| Day 119 | 3 | 0.0073 | 0.0436 | 2 | 0.0083 | 0.0144 | 3 | 0.0117 | 0.0294 | 3 | 0.0106 | 0.2400 |

Nobs = number of observed values above cut point

Note: no anti-CDP7657 observed values above cut point at any visits for all placebos (n=7)

Note: Presence of drug interferes with measurement of anti-CDP7657 antibodies in this assay Study design SL0014

Fig. 3

Clinical response in study SL0014 as measured by SRI4 and BICLA indices

| SRI4 | Placebo | CDP7657 | Total |
|---|---|---|---|
| Responder | 1 | 5 | 6 |
| Non-Responder | 6 | 7 | 13 |
| Total | 7 | 12 | 19 |
| Responder Rate | 14% | 42% | |

| BICLA | Placebo | CDP7657 | Total |
|---|---|---|---|
| Responder | 1 | 5 | 6 |
| Non-Responder | 6 | 6 | 12 |
| Total | 7 | 12 | 19 |
| Responder Rate | 14% | 45% | |

Clinical response in study SL0014 as measured by SLEDAI Response Index 50 (median change from baseline)

Fig. 5 The plasma exposure over a 20 week for single 60mg doses vs the dosing regimen used in subjects in SL0014.

Fig. 6
Pharmacokinetic data for the single and multiple-dose regimens illustrated in Figure 5.

| | 60 mg/kg single dose | 30 mg/kg + 5 x 15 mg/kg every 2 weeks |
|---|---|---|
| Cmax | 1077 (880-1344) | 541 (435-666) |
| $AUC_{(0-28d)}$ | 9846 (8276-11673) | 6665 (5578-7819) |
| $AUC_{(0-42d)}$ | 11143 (9183-13675) | 9790 (8137-11664) |
| $AUC_{(0-56d)}$ | 11723 (9495-14681) | 12905 (10640-15540) |
| $AUC_{(0-70d)}$ | 12020 (9715-15276) | 16011 (13136-19442) |
| $AUC_{(0-inf)}$ | 12329 (9776-15887) | 21694 (17127-27853) |
| % time concentration >100 µg/mL | 34 (27-45) | 90 (84-101) |

Fig. 7

Baseline Characteristics of Subjects Treated in Study SL0014

| Variable | Statistic | Placebo (N=8) | CDP7657 (N=16) | All subjects (N=24) |
|---|---|---|---|---|
| Age (years) | Mean (Min, Max) | 40.1 (18, 59) | 41.8 (29, 61) | 41.3 (18, 61) |
| BMI (kg/m2) | Mean (Min, Max) | 25.0 (18.7, 33.2) | 23.8 (16.7, 41.8) | 14.2 (16.7, 41.8) |
| Race | White, n (%) | 8 (100) | 15 (93.8) | 23 (95.8) |
| Gender | Female / Male (n) | 8 / 0 | 13 / 3 | 21 / 3 |
| SLEDAI | Median (Min, Max) | 8 (4, 14) | 10 (2, 16) | 9 (2, 16) |
| Ads DNA (U/mL) | Median (Min, Max) | 16 (1, 90) | 10 (1, 475) | 13 (1, 475) |
| Complement C4 (mg/L) | Median (Min, Max) | 215 (40, 330) | 145 (30, 420) | 150 (30, 420) |
| IgG (g/L) | Median (Min, Max) | 10.8 (4.7, 13.8) | 12.9 (5.6, 19.6) | 12.2 (4.7, 19.6) |
| BILAG | Grade A or B (n) | 7 | 11 | 18 |
| Concomitant medication | | | | |
| Corticosteriods | n | 7 | 14 | 21 |
| Immunosuppressants | n | 1 | 2 | 3 |
| Antimalarials | n | 4 | 3 | 7 |

Fig. 8

Summary of adverse events, by treatment group, in Study SL0014

| Category | Placebo | Study drug |
|---|---|---|
| | All N=8 n (%) E | All N=16 n (%) E |
| Any TEAEs | 5 (62.5) 23 | 14 (87.5) 56 |
| Serious TEAEs | 0 | 0 |
| Withdrawals due to TEAEs | 0 | 1 (6.3) 1 |
| Drug-related TEAEs | 3 (37.5) 4 | 4 (25.0) 9 |
| Severe TEAEs | 1 (12.5) 2 | 0 |
| Infection TEAEs | 3 (37.5) 5 | 9 (62.5) 15 | n = number of subjects, E = number of events. Percentages are % of subjects.

TREATMENT OF AUTOIMMUNE DISORDERS WITH CD154 ANTIBODIES

CROSS-REFERENCE TO RELATED APPLICATIONS

This application is a continuation of U.S. application Ser. No. 15/547,223, filed Jul. 28, 2017, which is the U.S. national stage application of International Patent Application No. PCT/EP2015/059095, filed Apr. 27, 2015.

The Sequence Listing for this application is labeled "Seq-List.txt" which was created on Jun. 28, 2017 and is 8 KB. The entire content of the sequence listing is incorporated herein by reference in its entirety.

FIELD OF THE INVENTION

The present invention relates to the treatment of autoimmune and inflammatory diseases, in particular the treatment of systemic lupus erythematosus with an antibody or antibody fragment binding specifically to CD154.

BACKGROUND OF THE INVENTION

Autoimmune diseases classically comprise more than 80 chronic diseases that affect about 5%-8% of the general population. There has been considerable progress made in understanding the immune system during recent decades, resulting in a better appreciation of the role of costimulatory molecules such as CD40 and its ligand CD154. Furthermore, a role for such molecules in the pathogenesis of much commoner diseases such as atherosclerosis is also emerging, which could greatly expand the applicability of therapies targeting this molecule.

CD154 is expressed on activated T lymphocytes and, through interactions with its receptor CD40, plays a pivotal role in regulating the interplay between T cells and other cell types. The CD154/CD40 pair is known to mediate cognate T cell help for B cells, resulting in increased B-cell proliferation and differentiation, antibody production and isotype class switching. CD154 also promotes the formation of germinal centers in lymph nodes and B-cell survival. CD154 therefore contributes to the potentiation of autoimmune diseases and holds significant promise as a therapeutic target in autoimmune disease such as systemic lupus erythematosus (SLE), rheumatoid arthritis, ankylosing spondylitis, lupus nephritis, Goodpasture's disease, Sjögren's syndrome, polymyositis, dermatomyositis, psoriasis, temporal arteritis, Churg-Strauss syndrome, multiple sclerosis, Guillain-Barré syndrome, transverse myelitis, myasthenia gravis, Addison's disease, thyroiditis, coeliac disease, ulcerative colitis, sarcoidosis, hemolytic anemia, idiopathic thrombocytopenic purpura, Behçet's disease, primary biliary cirrhosis and autoimmune diabetes, and blockade of CD154 has been shown to be highly efficacious in several inflammatory and autoimmune model systems. CD154 has also been suggested to play a role in the inflammatory aspects of atherosclerosis and neurodegenerative disorders.

CD154, also known as CD40 ligand (CD40L), previously referred to as gp39, TRAP, or TBAM, is a 39 kDa type II membrane glycoprotein of the TNF family. CD154 polypeptide of 261 amino acids, consisting of a 215 amino acids extracellular domain, a 24 amino acids transmembrane region, and a 22 amino acids cytoplasmic tail. Like other members of the TNF-family, CD154 forms a trimeric structure and promotes as such trimerization of the receptor, namely, CD40. The CD154/CD40 interaction is stabilized by charged residues, namely, the basic chains on CD154 and the acidic ones on CD40.

Hu5c8 (also known as BG-9588, or replizumab), a humanized monoclonal $IgG_1$ antibody against human CD154, was evaluated in clinical trials for a range of autoimmune diseases. Results from a phase 2 study in patients with systemic lupus erythematosus (SLE) were encouraging, with significant reductions in disease biomarkers, including circulating levels of autoantibodies, as well as marked increases in C3 levels. However, despite this promising evidence of clinical effect, further development of hu5c8 was discontinued because of an increased incidence of treatment-emergent cardiovascular thrombotic events. Hu5c8 was administered intravenously at a dose of 20 mg/kg given every 2 weeks for three doses, and then every 4 weeks for a further four doses (total seven doses) (Boumpas et al, Arthritis Rheum. 2003 March; 48(3):719-27) The mechanism by which hu5c8 induces thrombotic effects in humans remains unclear, although increased platelet activation has been demonstrated following exposure to hu5c8 in vitro (Meyer et al., Blood (ASH Annual Meeting Abstracts) 2006 108: Abstract 1516).

Systemic lupus erythematosus (SLE) has been classified as an autoimmune disease that may involve many organ systems, as an inflammatory multisystem rheumatic disorder, or as a collagen vascular disease. In Europe and the United States of America, estimates of the number of affected individuals range from 24 to 65 cases per 100,000 population in some studies. Predisposing factors for lupus include Asian or African race, and female gender. 90% of patients with lupus are female and the onset of symptoms usually occurs between the ages of 15 and 50 years. Systemic lupus erythematosus appears not to be a homogeneous disease, but a group of related syndromes, with widely varying presentations, degrees of body system involvement, and clinical course. Clinical features commonly seen in SLE are blood and lymphatic disorders (lymphadenopathy), cardiac disorders (e.g. cardiomyopathy, pericardial effusion, pericarditis), eye disorders (e.g. keratoconjunctivitis sicca), gastrointestinal disorders (e.g. mouth ulceration, pancreatitis, peritonitis, pharyngitis), general disorders (e.g. malaise, fatigue, pyrexia, weight decrease), nervous system disorders (e.g. cerebrovascular accident, cognitive disorder, migraine, headache, peripheral neuropathy), musculoskeletal and connective tissue disorders (e.g. arthralgia, arthritis (not erosive or destructive), fibromyalgia, fracture, myositis, osteonecrosis, osteoporosis, osteopenia), psychiatric disorders (e.g. affective disorder, anxiety, depression, psychosis, neurosis, mental disorder due to a general medical condition, psychotic disorder), renal and urinary disorders (e.g. lupus nephritis, nephrotic syndrome), respiratory, thoracic, and mediastinal disorders (e.g. pleurisy, pneumonitis, pulmonary hypertension), skin and subcutaneous tissue disorders (e.g. alopecia, cutaneous lupus erythematosus, dermatitis, generalised erythema, livedo reticularis, panniculitis, rash maculo-papular, systemic lupus erythematosus rash, urticaria) and vascular disorders (e.g. hypertension, Raynaud's phenomenon, telangiectasis, thrombocytopenia, thrombophlebitis, vasculitis). Additionally, most SLE patients present with abnormal antibody patterns, including the presence of anti-nuclear- (ANA) and anti-double stranded DNA (anti-dsDNA) antibodies.

The clinical course of SLE is episodic, with flares recurring upon increasing underlying disability and organ damage. Corticosteroids are the cornerstone of treatment but are associated with an extensive number of side effects most frequently seen during long-term use. Other drugs used in the setting of lower-level activity include analgesics, non-steroidal anti-inflammatory drugs (NSAIDs), local steroids, and antimalarial drugs (e.g., chloroquine or hydroxychloroquine), with common supportive medications including vasodilators (calcium channel blockers, angiotensin-converting enzyme [ACE] inhibitors) for renal hypertension or Raynaud's syndrome, local treatments for rashes or sicca syndromes, transfusions, intravenous (i.v.) globulin for cytopenias, anticonvulsants, antimigraine medications, anticoagulants for recurrent thromboses, and antidepressants. High-dose corticosteroids, e.g., 0.5 to 1.0 mg/kg/day oral prednisone (or equivalent) or 500 mg to 1 g daily pulse i.v. methylprednisolone, are used to manage acute SLE flares, with immunosuppressants (e.g., azathioprine, cyclophosphamide, methotrexate, mycophenolate mofetil, leflunomide) generally used in moderate and severe cases when other treatments are ineffective or to limit or prevent long-term major organ damage from the disease or corticosteroid use ('steroid-sparing'). This present therapeutic armamentarium is inadequate because of limited efficacy and/or adverse events profile. Despite the high medical need for new effective therapies of SLE with an good safety profile the development of such therapies has proven to be particularly difficult and many therapeutic candidates have failed (Eisenberg, 2009).

The CD40/CD154 costimulatory pathway has also been implicated in the pathogenesis of neurodegenerative and neuromuscular disorders and treatment with compounds that interfere with the pathway appear to be useful for treatment of neurodegenerative and neuromuscular disorders (WO 2010/065819, the content of which is incorporated herein in its entirety).

Neurodegenerative and neuromuscular disorders include Alzheimer's Disease, Parkinson's Disease, Amyotrophic Lateral Sclerosis, Myasthenia Gravis, Multifocal Motor Neuropathy, Primary Lateral Sclerosis, Spinal Muscular Atrophy, Kennedy's Disease, and Spinocerebellar Ataxia.

Amyotrophic lateral sclerosis (ALS), sometimes called Lou Gehrig's Disease, is a progressive, fatal, neurological disorder characterized by muscle fiber atrophy resulting from the degeneration of motor neurons in the spinal column and brain. ALS affects approximately 30,000 US citizens with only about 10% of the cases being classified as the familial form of ALS. Although ALS is characterized by loss of motor neurons in the spinal cord resulting in muscle atrophy, the disease also manifests itself with changes in axon transport, protein aggregation, excitotoxicity, astrocytosis, mitochondrial dysfunction, microglial activation, and synaptic remodeling. Microglial activation, astrocytosis and the presence of infiltrating inflammatory cells from the periphery has been well described. There is accumulation of IgG immunoreactive deposits in the spinal cord of ALS patients, infiltration of lymphocytes, dendritic cells, monocytes, and macrophages into the spinal cord in ALS. Although the role of infiltrating immune cells is poorly understood, recent work would suggest that infiltrating T cell populations are neuroprotective and not cytotoxic. Although ALS has an immune component mediated by activation of microglia and astrocytes it is not considered to be an autoimmune disorder. Unlike diseases such as rheumatoid arthritis or systemic lupus erythematosus in which involvement of specific immune modulatory pathways (e.g., the costimulatory pathway) has been described, involvement of such pathways has not been described for ALS.

There is a need in the art for new effective treatments of autoimmune, inflammatory, neurodegenerative and neuromuscular disorders. The CD40-CD40L(CD154) interaction pathway has been demonstrated to be relevant for the pathophysiology autoimmune, inflammatory, neurodegenerative and neuromuscular disorders. There is a need for new treatments of autoimmune, inflammatory, neurodegenerative and neuromuscular disorders with antibodies or antibody fragments binding specifically to CD154 administered at a safe and effective dose.

SUMMARY OF THE INVENTION

The following summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. With respect to aspects of the invention described or claimed with "a" or "an", it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature. Where the term "about" is used the application also discloses employing the exact value specified. Where point values are referred to, the application also discloses about such values being employed, the same being the case for endpoints of ranges.

Clinical phase I randomized, double-blind, placebo-controlled, studies of the safety and tolerability of a monovalent PEGylated Fab' binding specifically to CD154 (CDP7657) in serologically-positive patients afflicted with systemic lupus erythematosus (SLE) were performed. The monovalent PEGylated Fab' binding specifically to CD154 was well tolerated, and no thromboembolic side effects were observed.

As a result of the study a new dosing regimen has now been found for an antibody or antibody fragment binding specifically to CD154 in the treatment of autoimmune and inflammatory diseases, such as SLE, or a neurodegenerative or neuromuscular disease.

In one embodiment the invention provides an antibody or antibody fragment binding specifically to CD154 for use in a method for treating an autoimmune, inflammatory, neurodegenerative or neuromuscular disorder in a mammalian subject, which method comprises administering an initial loading dose of about 20-60 mg/kg of antibody or antibody fragment binding specifically to CD154 to a subject in need of such treatment; and about 2 weeks after the initial loading dose administering a further dose or doses of about half of the initial loading dose with a frequency of about once every other week of antibody or antibody fragment binding specifically to CD154 to the subject in need of such treatment.

In another embodiment of the invention the antibody or antibody fragment binding specifically to CD154 is administered to the patient in need thereof at least for 12 weeks.

In another embodiment of the invention the antibody or antibody fragment binding specifically to CD154 is a neutralizing antibody or antibody fragment. The antibody or antibody fragment binding specifically to CD154 according to the first, second or third embodiment of the invention preferably has a dissociation constant for monovalent binding to CD40 of $K_D \leq 4.55$ pM as determined by surface plasmon resonance.

In another embodiment of the invention the antibody or antibody fragment binding specifically to CD154 contains a light chain variable region (LCVR) having a CDR1, a CDR2 and a CDR3 comprising the amino acid sequence of SEQ ID NOs:1, 2 and 3, respectively, and a heavy chain variable region (HCVR) having a CDR1, a CDR2 and a CDR3 comprising the amino acid sequence of SEQ ID NOs: 4, 5 and 6, respectively.

In further embodiments of the invention the antibody or antibody fragment binding specifically to CD154 contains the VL chain sequence shown in SEQ ID NO:7 and the VH chain sequence shown in SEQ ID NO:8 or the antibody or antibody fragment binding specifically to CD154 has the light chain sequence shown in SEQ ID NO:9 and the heavy chain sequences shown in SEQ ID NO:10.

In further embodiments of the invention the antibody or antibody fragment binding specifically to CD154 according to any of the embodiments of the invention is a monovalent Fab' having the light chain sequence shown in SEQ ID NO:9 and the heavy chain sequences shown in SEQ ID NO:10 which is PEGylated at a cysteine in the modified hinge region. Preferably, the monovalent Fab' having the light chain sequence shown in SEQ ID NO:9 and the heavy chain sequences shown in SEQ ID NO:10 according to the eleventh embodiment invention has a maleimide group covalently linked to a single thiol group in the modified hinge region; a lysine residue is covalently linked to the maleimide group; and a methoxypoly(ethyleneglycol) polymer having a molecular weight of approximately 20 KDa is attached to each of the amine groups on the lysine residue. The total molecular weight of the entire PEG covalently linked to the monovalent Fab' is therefore approximately 40 KDa.

BRIEF DESCRIPTION OF THE FIGURES

FIG. 1 shows the incidence of anti-drug antibodies in subjects with SLE. Very weak anti-drug antibody responses (i.e. very close to cut point) were observed across all doses for subjects with SLE. The highest response in dose group 60 mg/kg where the ADA measured increased as drug cleared. Assay cut point is 0.0063 units/mL (where 1 unit/mL equates to 1 μg/mL calibrator). It was found that overall anti-drug antibodies which developed to a very low level in patients with SLE did not impact on the pharmacokinetics of the monovalent PEGylated Fab' binding specifically to CD154.

FIG. 3 shows the headline results from Study SL0014, in which the two key efficacy outcomes
  a minimum 4-point improvement in SLEDAI-2K Responder Index (SRI-4), and
  response according to the British Isles Lupus Assessment Group (BILAG)-based Composite Lupus Assessment (BICLA)
    both demonstrate consistent and substantially higher response rates for subjects receiving CDP7657 under the described dosing regimen than for those receiving placebo treatment.

FIG. 6 shows the pharmacokinetic data from the two dosing regimens illustrated in FIG. 5, and confirms the success of the Study SL0014 regimen in maintaining exposure levels above 100 μg/mL for at least 90% of the time.

FIG. 7 shows the baseline demographic characteristics of the subjects randomised to the active and placebo treatment groups, and demonstrates that a well-balanced randomization was achieved.

FIG. 8 shows the incidence and character of the adverse events seen during Study SL0014, which indicate little substantial difference between active and placebo treatment groups. There were no events of, or suggestive of, thromboembolism.

DETAILED DESCRIPTION OF THE INVENTION

Figure 2:
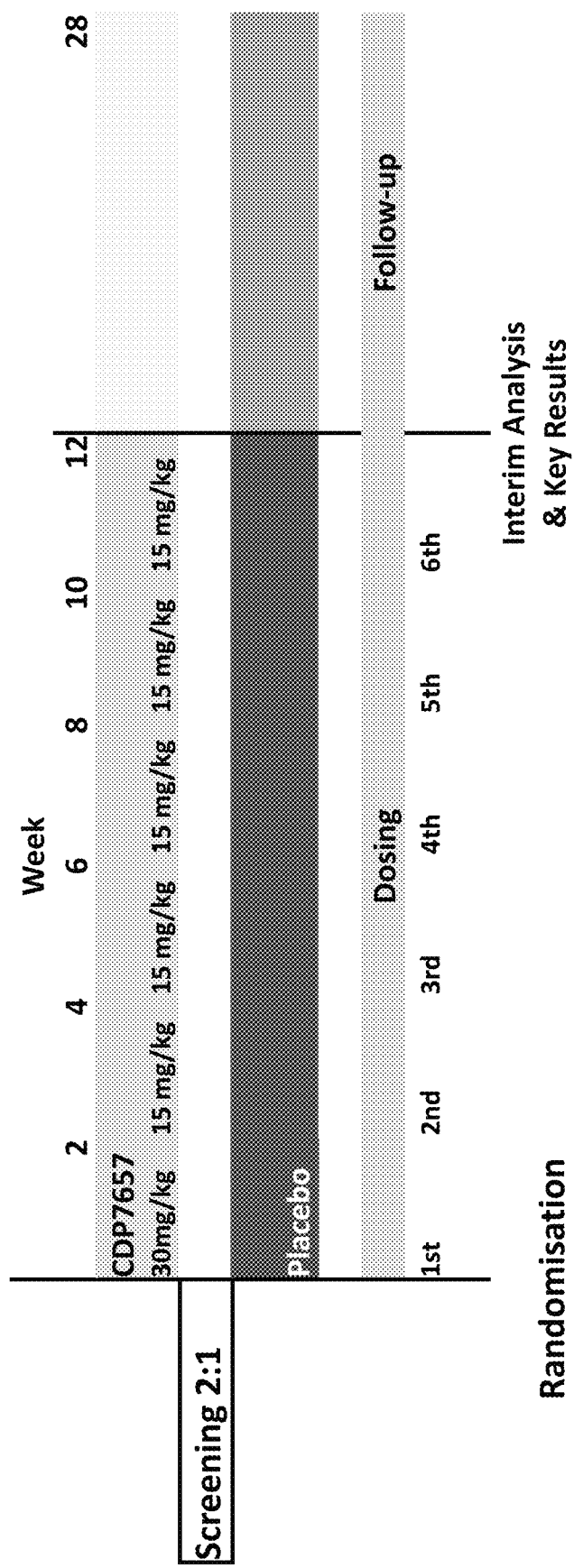
FIG. 2 shows the dosing regimen followed during the initial proof-of-concept clinical study with CDP7657 (Study SL0014), wherein the principle of using a larger loading dose followed by regular, equal maintenance doses was established.
Figure 4:
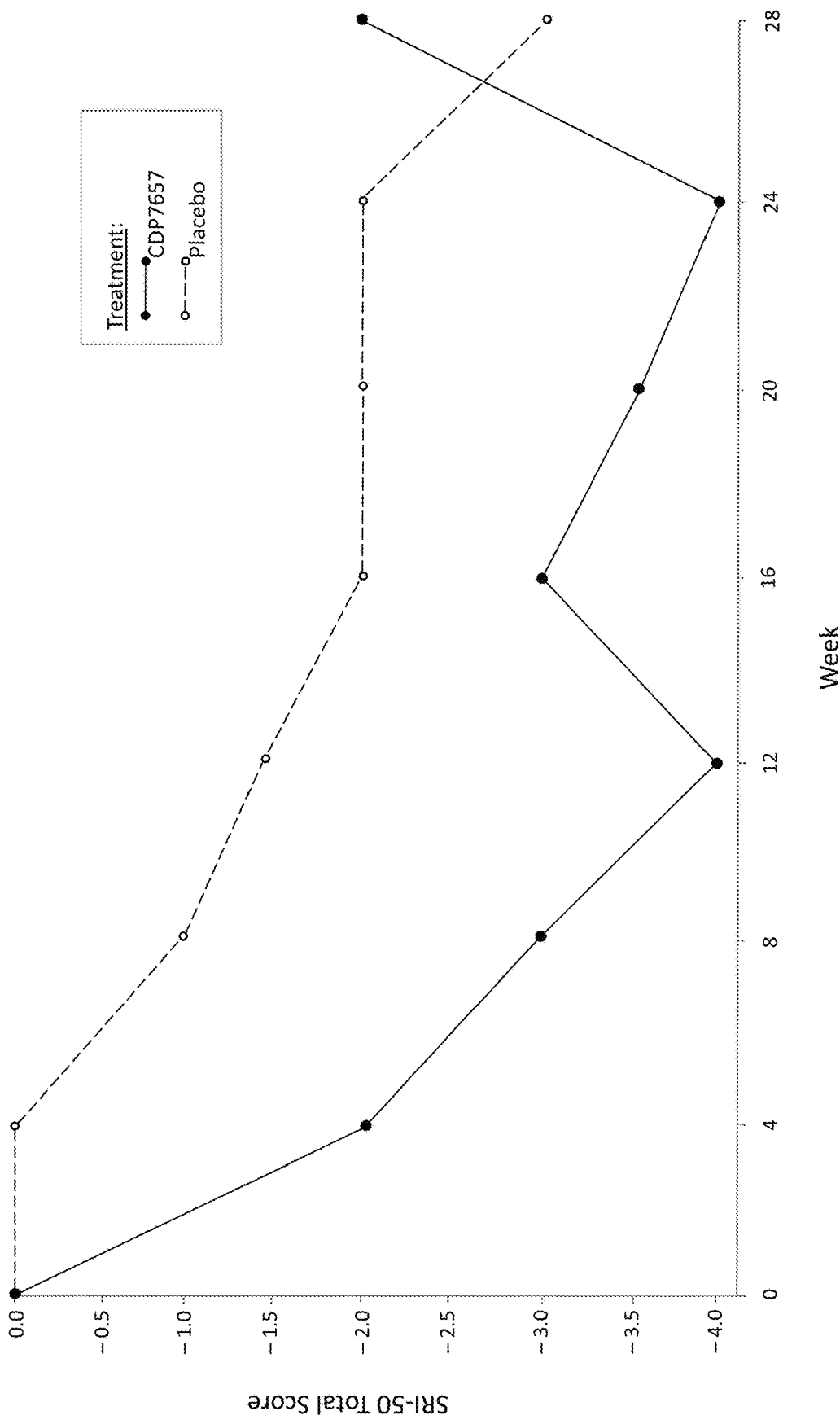
FIG. 4 shows the substantial clinical response to CDP7657 that was seen within one month of initiation of treatment, which continued to grow until the end of treatment at 3 months, and was sustained for a further 3 months thereafter.
Figure 5:
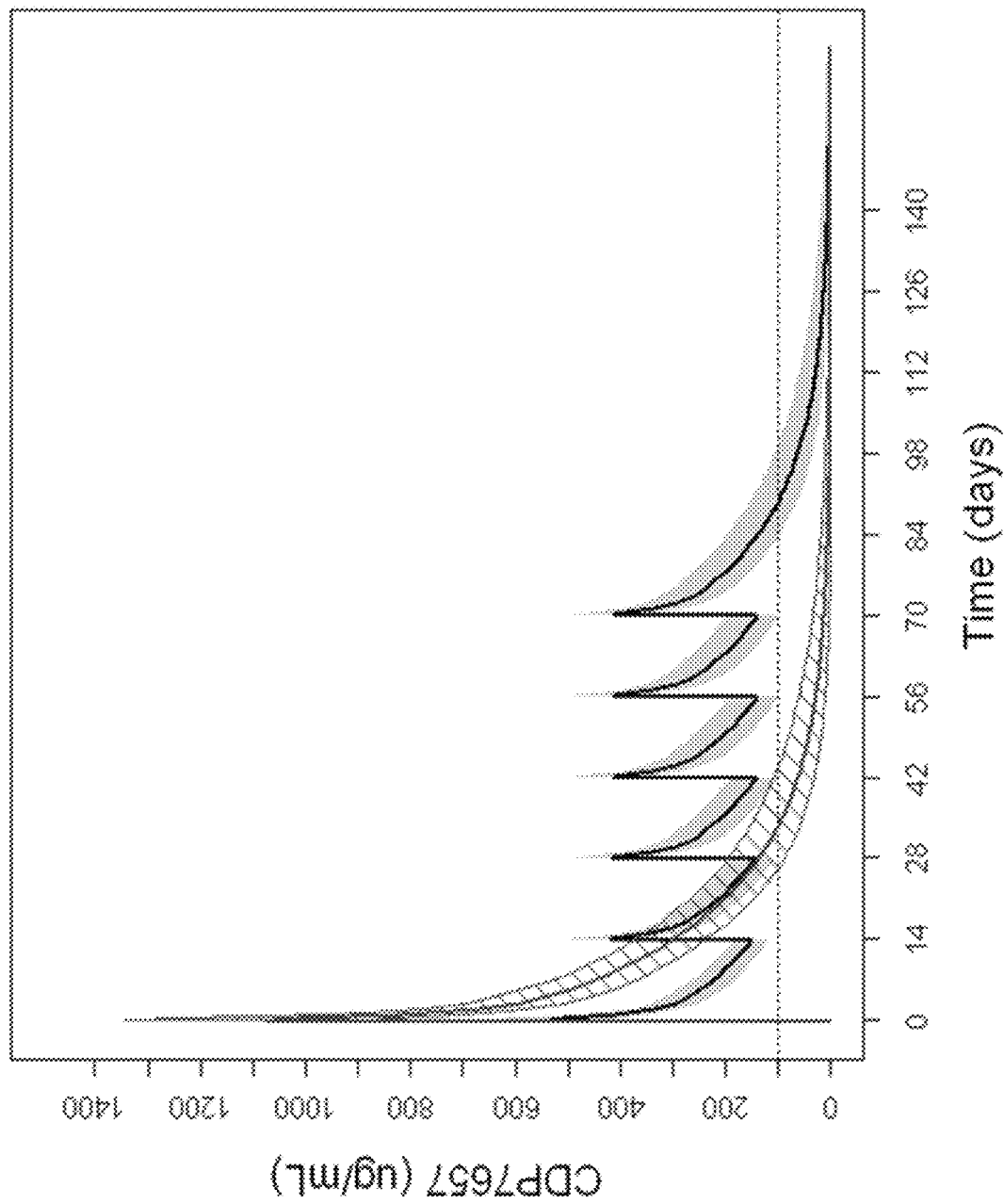
FIG. 5 shows the different plasma exposure profiles for subjects administered a single 60 mg dose of CDP7657, as compared to the dosing regimen used in Study SL0014. The latter produces rapid attainment and then consistent maintenance of plasma levels above the indicated target of 100 μg/mL, while dosing continues.

This invention pertains to methods of treating an autoimmune or inflammatory disease or a neurodegenerative disease in which the administration of an antibody or antibody fragment binding specifically to CD154 is beneficial. Various embodiments of the invention relate to treatment of an autoimmune or inflammatory disease or a neurodegenerative disease with an antibody or antibody fragment binding specifically to CD154, particularly CDP7657.

In order that the present invention may be more readily understood, certain terms are first defined.

The term "antibody" or "antibodies" as used herein, refers to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. A heavy chain constant region can also have a fourth constant domain, CH4. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino terminus to carboxy-terminus in the following order: FR1, CDR1, FR2, CDR2, FR3, CDR3, FR4. The exact boundaries of these CDRs have been defined differently according to different systems. The system described by Kabat not only provides an unambiguous residue numbering system applicable to any variable region of an antibody, but also provides precise residue boundaries defining the three CDRs. These CDRs may be referred to as Kabat CDRs. Chothia et al. found that certain sub-portions within Kabat CDRs adopt nearly identical peptide backbone conformations, despite having great diversity at the level of amino acid sequence (Chothia et al. (1987) Mol. Biol. 196:901-917; Chothia et al. (1989) Nature 342:877-883). These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5):732-45. Still other CDR boundary definitions may not strictly follow one of the herein described systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. The term immunoglobulin or immunoglobulins is used synonymously with "antibody" or "antibodies", respectively. The term "antibody" or "antibodies" as used herein includes but is not limited to recombinant antibodies that are generated by recombinant technologies as known in the art. An "antibody" or "antibodies" can be of any origin including from mammalian species such as human, non-human primate (e.g. human such as from chimpanzee, baboon, rhesus or cynomolgus monkey), rodent (e.g. from mouse, rat, rabbit or guinea pig), goat, bovine or horse species; or of bird species such as chicken antibodies or of fish species such as shark antibodies. "Antibody" or "antibodies" include antibodies' of any isotype, including human isotypes IgA$_1$, IgA$_2$, IgD, IgG$_1$, IgG$_{2a}$, IgG$_{2b}$, IgG$_3$, IgG$_4$, IgE and IgM and modified variants thereof. The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens are also contemplated. Where the antigen is a polypeptide, it may be a transmembrane molecule (e.g. receptor) or ligand such as a growth factor or cytokine. Preferred molecular targets for antibodies encompassed by the present invention include CD polypeptides such as CD3, CD4, CD8, CD19, CD20, CD22, CD34, CD38, CD40 and CD154; FcRN; OX40; members of the HER receptor family such as the EGF receptor, HER2, HER3 or HER4 receptor; cell adhesion molecules such as LFA-1, Mac1, p150,95, VLA-4, ICAM-1, VCAM and av/b3 integrin including either α or β subunits thereof (e.g. anti-CD11a, anti-CD18 or anti-CD11 b antibodies); chemokines and cytokines or their receptors such as IL-1 α and β, IL-2, IL-6, the IL-6 receptor, IL-7, IL-12, IL-13, IL-17 forms, IL-18, IL-21, IL-23, TNFα and TNFβ; growth factors such as VEGF; IgE; blood group antigens; flk2/flt3 receptor; obesity (OB) receptor; mpl receptor; CTLA-4; polypeptide C; etc.

The term "antibody fragment" or "antibody fragments" as used herein, refers an a naturally occurring antibody which lacks on or more domains or one or more amino acids. Typically, antibody fragment contains the entire antigen binding or variable region thereof of such naturally occurring antibody. Examples of antibody fragments include any antibody that lacks the or has no Fc portion. Examples of antibody fragments include also Fab, Fab', F(ab')$_2$, Fv and scFv fragments; diabodies; triabodies; tetrabodies; minibodies; antibodies consisting essentially of a single, two or three immunoglobulin domain(s) such as Domain Antibodies™; single-chain antibodies; bispecific, trispecific, tetraspecific or multispecific variants of any of the above. The term "antibody fragment" or "antibody fragments" as used herein also refers to camelid antibodies (e.g. from camels or llamas such as Nanobodies™) and derivatives thereof. Antibodies fragments are well known in the art (Holliger and Hudson, 2005). Various techniques have been developed for the production of antibody fragments and are known in the art (Glover and Humphreys, 2004). The term "antibody fragment" or "antibody fragments" as used herein, comprises human, humanized, primatized and chimeric antibody fragments.

The term "BILAG score" or "BILAG" index as used herein, refers to the British Isles Lupus Assessment Group score and index, respectively (Symmons D P et al. Q J Med. 1988 November; 69(259):927-37). The BILAG index was used to assess efficacy of treatment in patients with SLE in study SL0007. It is a comprehensive index for measuring SLE disease activity. The 2004 version of the BILAG index was used for the studies. This version consists of 86 questions in 8 body systems (general, mucocutaneous, neurological, musculoskeletal, cardiovascular and respiratory, vasculitis, renal, and hematological). Some of the questions were based on the patient's history, some on examination findings, and others on laboratory results. Each body system score ranges from E to A, with A being the most severe disease activity. The interpretation of body system scores are as follows: A ("Active")=severely active disease (sufficient to require disease-modifying treatment, for example, greater than 20 mg/day of prednisone, immunosuppressants, cytoxics); B ("Beware")=moderately active disease (requires only symptomatic therapy, for example, less than or equal to 20 mg/day of prednisone or antimalarial drugs; C ("Contentment")=mild stable disease (no indication for changes in treatment); D=previously active disease—but none currently; E=no prior disease activity. When the BILAG alphabetic organ body system scores are converted to numeric values and summed (using the rule where each BILAG A=9, each BILAG B=3, each BILAG C=1, and each BILAG D or E is worth 0), this is referred to as a Total BILAG score.

The term "CDP7657" as used herein, refers to a monovalent PEGylated Fab' binding specifically to CD154 which is disclosed in WO 2008/118356 (incorporated herein in its entirety). CDP7657 has a light chain variable region (LCVR) with the CDR1, CDR2 and CDR3 having the amino acid sequence of SEQ ID NOs:1, 2 and 3, respectively, and a heavy chain variable region (HCVR) with the CDR1, CDR2 and CDR3 having the amino acid sequence of SEQ ID NOs: 4, 5 and 6, respectively. CDP7657 has the VL chain sequence shown in SEQ ID NO:7 and the VH chain sequence shown in SEQ ID NO:8. CDP7657 has the light chain sequence shown in SEQ ID NO:9 and the heavy chain sequences shown in SEQ ID NO:10. CDP7657 is PEGylated at a cysteine in the modified hinge region as described in WO 2008/118356.

The term "combination therapy", as used herein, refers to the administration of two or more therapeutic substances, e.g., an antibody or antibody fragment binding specifically to CD154 and cortisol. The cortisol may be administered concomitant with, prior to, or following the administration of an Antibody or antibody fragment binding specifically to CD154.

The term "every other week", as used herein, in connection with treatment with, administration of or dosing of an antibody or antibody fragment binding specifically to CD154 according to the invention, or a composition comprising same, refers to the administration of the antibody or antibody fragment binding specifically to CD154 according to the invention or said composition every 9-19 days, more preferably, every 11-17 days, even more preferably, every 13-15 days, and most preferably, every 14 days.

The term "$K_D$", as used herein, is intended to refer to the dissociation constant of a particular antibody-antigen interaction. The dissociation constant can refer to monovalent binding or bivalent binding. Preferably, the dissociation constant is determined by surface plasmon resonance.

The term "neutralizing antibody", as used herein (or an "antibody that neutralized CD154 activity"), is intended to refer to an antibody whose binding to CD154 results in inhibition of the biological activity of CD154. This inhibition of the biological activity of CD154 can be assessed by measuring one or more indicators of CD154 biological activity. These indicators of CD154 biological activity can be assessed by one or more of several standard in vitro or in vivo assays known in the art. For example, in vitro assays could measure the capacity of antibodies to inhibit the binding of a purified CD40 protein to CD40L-expressing cells or cell lines or an assay of T-cell-dependent B-cell activation, involving co-culture of CD40L-expressing T-cell or T-cell line with B cells or a B cell line and monitoring intercellular adhesion molecule 1 (ICAM-1) expression on the latter cells. In vivo assays could include investigating the immune response to an antigen such as tetanus toxoid or keyhole limpet hemocyanin in a suitable species such as the non-human primate if the antibody recognizes this species or in mice if the antibody recognizes this species. If the antibody does recognize mouse CD40L, then it could be assessed in a mouse model of SLE such as the NZB/W or MRL/lpr mice.

The term "PEGylation", "polyethylene glycol" or "PEG", as used herein, refers to the attachment, e.g. through covalent bonding, of a polyalkylene glycol compound or a derivative thereof, with or without coupling agents or derivatization with coupling or activating moieties (e.g., with thiol, triflate, tresylate, azirdine, oxirane, or preferably with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types: dextran, colominic acids, or other carbohydrate based polymers, polymers of amino acids, and biotin and other affinity reagent derivatives.

The term "SLEDAI score" or "SLEDAI" index refers to the Systemic Lupus Erythematosus Disease Activity score/index, respectively (Hawker et al., J Rheumatol. 1993).

The term "SRI score" or "SRI" index refers to the Systemic Lupus Erythematosus Responder Indexscore/index (Furie R A et al., Arthritis Rheum. 2009).

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, NJ). For further descriptions, see Example 1 and Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

In a first embodiment the invention provides an antibody or antibody fragment binding specifically to CD154 for use in a method for treating an autoimmune, inflammatory, neurodegenerative or neuromuscular disorder in a mammalian subject, which method comprises:
 (a) administering an initial loading dose of about 20-60 mg/kg of antibody or antibody fragment binding specifically to CD154 to a subject in need of such treatment; and
 (b) about 2 weeks after the initial loading dose administering a further dose or doses of about half of the initial loading dose with a frequency of about once every other week of antibody or antibody fragment binding specifically to CD154 to the subject in need of such treatment. The initial loading dose can be about 20 mg/kg, 25 mg/kg, 30 mg/kg, 35 mg/kg, 40 mg/kg, 45 mg/kg, 50 mg/kg, 55 mg/kg or 60 mg/kg. The further dose can be about 10 mg/kg, 12.5 mg/kg, 15 mg/kg, 17.5 mg/kg, 20 mg/kg, 22.5 mg/kg, 25 mg/kg, 27.5 mg/kg or 30 mg/kg.

In the second embodiment of the invention the antibody or antibody fragment binding specifically to CD154 according to the first embodiment of the invention is administered to the patient in need thereof at least for 12 weeks.

In the third embodiment of the invention the antibody or antibody fragment binding specifically to CD154 according to the first or second embodiment of the invention is a neutralizing antibody or antibody fragment.

In the fourth embodiment of the invention the antibody or antibody fragment binding specifically to CD154 according to the first, second or third embodiment of the invention has a dissociation constant for monovalent binding to CD40 of $K_D \leq 4.55$ pM as determined by surface plasmon resonance.

In the fifth embodiment of the invention the antibody or antibody fragment binding specifically to CD154 according to the first, second, third or fourth embodiment of the invention contains a light chain variable region (LCVR) having a CDR1, a CDR2 and a CDR3 comprising the amino acid sequence of SEQ ID NOs:1, 2 and 3, respectively, and a heavy chain variable region (HCVR) having a CDR1, a CDR2 and a CDR3 comprising the amino acid sequence of SEQ ID NOs: 4, 5 and 6, respectively.

In the sixth embodiment of the invention the antibody or antibody fragment binding specifically to CD154 according to the first, second, third, fourth or fifth embodiment of the invention contains framework regions for variable light (VL) chain preferably are from the Vκ1 human germ line family, more preferably from the Vκ1 2-1-(1) O12 V-region and most preferably from the VL chain framework sequences shown in SEQ ID NO:7. The framework regions for variable heavy (VH) chain are preferably from the VH4 chain human germline family, more preferably from the VH4 1-1 4-59 sequence and most preferably from the VH framework sequences shown in SEQ ID NO:8.

In the seventh embodiment of the invention the antibody or antibody fragment binding specifically to CD154 according to the first, second, third, fourth, fifth or sixth embodiment of the invention exhibits monovalent binding to CD40, and preferably has only one binding site that binds specifically CD154. Preferably, the antibody or antibody fragment binding specifically to CD154 is a VH domain or domain antibody (dAb), Fab, Fab', Fv, Fab-Fv, Fab-dsFv, Fab-Fv-Fv, Fd, HL, dsHL, LH, dsLH, a single-chain antibody (e.g., scFv, scFab, and scFabΔC) or other monovalent fragment or antibody derivative, or a bispecific or multispecific antibody exhibiting specific and monovalent binding to CD154, such as a DVD-Ig, Triomab™, F(ab)$_2$, F(ab')$_2$, F(ab')$_3$, (Fab-Fv)$_2$-Fc or tribody.

In the eighth embodiment of the invention the antibody or antibody fragment binding specifically to CD154 according to the first, second, third, fourth, fifth, sixth or seventh embodiment of the invention is a conjugate comprising any antibody or antibody fragment that specifically binds CD154 conjugated covalently or noncovalently, or directly or indirectly, to a functional moiety such as a carrier protein, a toxin or other effector molecule, or PEG, for example. The antibody or antibody fragment binding specifically to CD154 may be PEGylated, e.g. at one or more cysteine or lysine residues. In certain embodiments, antibody fragment binding specifically to CD154 is a Fab or Fab' fragment PEGylated via a maleimide linker. In further embodiments of the invention the antibody fragment binding specifically to CD154 is conjugated to a functional moiety which is a blocking moiety, a detectable moiety (e.g., fluorescent moiety, radioisotopic moiety, radiopaque moiety, etc., including a diagnostic moiety), and/or a therapeutic moiety (e.g., a cytotoxic agent, anti-inflammatory agent, immunomodulatory agent, anti-infective agent, anti-cancer agent, anti-neurodegenerative agent, a radionuclide, etc.).

In the ninth embodiment of the invention the antibody or antibody fragment binding specifically to CD154 according to the first, second, third, fourth, fifth, sixth, seventh or eighth embodiment of the invention the antibody contains the VL chain sequence shown in SEQ ID NO:7 and the VH chain sequence shown in SEQ ID NO:8.

In the tenth embodiment of the invention the antibody or antibody fragment binding specifically to CD154 according to the first, second, third, fourth, fifth, sixth, seventh, eighth or ninth embodiment of the invention the antibody has the light chain sequence shown in SEQ ID NO:9 and the heavy chain sequences shown in SEQ ID NO:10.

In the eleventh embodiment of the invention the antibody or antibody fragment binding specifically to CD154 for use in a method for treating an autoimmune, inflammatory, neurodegenerative or neuromuscular disorder in a mammalian subject according to the first, second, third, fourth, fifth, sixth, seventh, eighth, ninth or tenth embodiment of the invention the antibody fragment is a monovalent Fab' having the light chain sequence shown in SEQ ID NO:9 and the heavy chain sequences shown in SEQ ID NO:10.

In the twelfth embodiment of the invention the monovalent Fab' having the light chain sequence shown in SEQ ID NO:9 and the heavy chain sequences shown in SEQ ID NO:10 according to the eleventh embodiment of the invention is PEGylated at a cysteine in a modified hinge region. Preferably, the monovalent Fab' having the light chain sequence shown in SEQ ID NO:9 and the heavy chain sequences shown in SEQ ID NO:10 according to the eleventh embodiment invention has a maleimide group covalently linked to a single thiol group in the modified hinge region; a lysine residue is covalently linked to the maleimide group; and a methoxypoly(ethyleneglycol) polymer having a molecular weight of approximately 20 KDa is attached to each of the amine groups on the lysine residue. The total molecular weight of the entire PEG covalently linked to the monovalent Fab' is therefore approximately 40 KDa.

In further embodiments the antibody or antibody fragment binding specifically to CD154 for use in a method for treating an autoimmune, inflammatory, neurodegenerative or neuromuscular disorder in a mammalian subject according to any of the embodiments of the invention are antibodies, antibody fragments or derivatives as described in WO 2008/118356 and WO 2006/030220 (the contents both of which are incorporated herein in its entirety).

The thirteenth embodiment of the invention is an antibody or antibody fragment binding specifically to CD154 for use in a method for treating an autoimmune, inflammatory, neurodegenerative or neuromuscular disorder in a mammalian subject according to the first, second, third, fourth, fifth, sixth, seventh, eighth, ninth, tenth, eleventh or twelfth embodiment of the invention methods for treating an autoimmune, inflammatory, neurodegenerative or neuromuscular disease wherein the autoimmune, inflammatory, neurodegenerative or neuromuscular disease is systemic lupus erythematosus (SLE), lupus nephritis, rheumatoid arthritis, seronegative spondyloarthropathies, psoriasis, psoriatic arthritis, scleroderma, Sjögren's syndrome, multiple sclerosis, type I diabetes, autoimmune uveitis and nephrotic syndrome or vasculitis.

In another embodiment antibody or antibody fragment binding specifically to CD154 according to any of the embodiments of the invention is for use in a method for treating systemic lupus erythematosus (SLE) wherein the subject treated with the antibody or antibody fragment binding specifically to CD154 achieves an improvement from baseline of one or more of the indices selected from SLEDAI, BILAG and Global Physician assessment. Thus, in one embodiment, the invention pertains to methods of treating a subject having SLE using the methods described herein wherein the subject achieves an improvement in one of these indices.

In another embodiment antibody or antibody fragment binding specifically to CD154 according to any of the embodiments of the invention is for use in a method for treating systemic lupus erythematosus (SLE) wherein the subject treated with the antibody or antibody fragment binding specifically to CD154 achieves a SLEDAI Responder Index 4 (SRI-4). Thus, in one embodiment, the invention pertains to methods of treating a subject having SLE using the methods described herein wherein the subject achieves a SLEDAI Responder Index 4.

In another embodiment antibody or antibody fragment binding specifically to CD154 according to any of the embodiments of the invention is for use in a method for treating systemic lupus erythematosus (SLE) wherein the subject treated with the antibody or antibody fragment binding specifically to CD154 achieves a 50% improvement from baseline of the SRI-50 index. Thus, in one embodiment, the invention pertains to methods of treating a subject having SLE using the methods described herein wherein the subject achieves a 50% improvement from baseline of the SRI-50 index.

In another embodiment antibody or antibody fragment binding specifically to CD154 according to any of the embodiments of the invention is for use in a method for treating systemic lupus erythematosus (SLE) wherein the subject treated with the antibody or antibody fragment binding specifically to CD154 achieves an increase of 20%, 30%, 40%, 50%, 75% or 90% from baseline or normalization of complement C3 and C4 concentration, or a reduction of 20%, 30%, 40%, 50%, 75% or 90% of anti-double stranded DNA titre in serum. Thus, in one embodiment, the invention pertains to methods of treating a subject having SLE using the methods described herein wherein the subject achieves an increase of 20%, 30%, 40%, 50%, 75% or 90% from baseline or normalization of complement C3 and C4 concentration, or a reduction of 20%, 30%, 40%, 50%, 75% or 90% of anti-double stranded DNA titre in serum.

In another embodiment antibody or antibody fragment binding specifically to CD154 according to any of the embodiments of the invention is for use in a method for treating systemic lupus erythematosus (SLE) wherein the subject treated with the antibody or antibody fragment binding specifically to CD154 reverts from seropositive to seronegative for anti-double stranded DNA antibodies. Thus, in one embodiment, the invention pertains to methods of treating a subject having SLE using the methods described herein wherein the subject reverts from seropositive to seronegative for anti-double stranded DNA antibodies.

In another embodiment the antibody or antibody fragment binding specifically to CD154 according to any of the embodiments of the invention is covalently linked to PEG through a thiol group of at least one cysteine residue located in an antibody or antibody fragment of this invention. Each PEG molecule attached to the antibody or antibody fragment may be covalently linked to the sulphur atom of a cysteine residue located in the antibody or antibody fragment. The covalent linkage will generally be a disulphide bond or, in particular, a sulphur-carbon bond. Where a thiol group is used as the point of attachment appropriately activated functional moieties, for example thiol selective derivatives such as maleimides and cysteine derivatives may be used. An activated PEG may be used as the starting material in the preparation of PEG-modified antibody fragments as described above. The activated PEG may be any PEG containing a thiol reactive group such as an halocarboxylic acid or ester, e.g. iodoacetamide, an imide, e.g. maleimide, a vinyl sulphone or a disulphide. In another embodiment the antibody fragment conjugate may comprise two PEG molecules with two maleimide molecules. Starting materials may be obtained commercially (for example from Nektar, formerly Shearwater Polymers Inc., Huntsville, AL, USA) or may be prepared from commercially available starting materials using conventional chemical procedures. Particular PEG molecules include methoxy-PEG-amine with a molecular weight of 20 KDa (obtainable from Nektar, formerly Shearwater; Rapp Polymere; and SunBio) and M-PEG-SPA (obtainable from Nektar, formerly Shearwater).

In another embodiment the antibody or antibody fragment binding specifically to CD154 is a modified Fab' fragment which is PEGylated, i.e. has PEG (poly(ethyleneglycol)) covalently attached thereto, e.g. according to the method disclosed in EP0948544 (see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545). In one example PEG is attached to a cysteine in the hinge region. In another example, a PEG modified Fab' fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20 KDa. The total molecular weight of the PEG attached to the Fab' fragment may therefore be approximately 40 KDa.

In another embodiment the antibody or antibody fragment binding specifically to CD154 according to any of the embodiments of the invention the PEG functional moiety is attached using the methods described in WO 98/25971 (the content of which is incorporated herein in its entirety) and WO 04/72116 (the content of which is incorporated herein in its entirety), whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20 KDa. The total molecular weight of the PEG attached to the antibody is therefore about 40 KDa.

Another embodiment of the invention is an antibody or antibody fragment binding specifically to CD154 for use in a method for treating an autoimmune, inflammatory, neurodegenerative or neuromuscular disorder in a mammalian subject according to any of the embodiments of the invention wherein the method comprises for intravenous, subcutaneous or intramuscular administration of the antibody or antibody fragment to the individual in need thereof. Subcutaneous administration is advantageous because the patient may self-administer a therapeutic substance, e.g., an antibody or antibody fragment binding specifically to CD154, which is convenient for both the patient and the health care provider.

In certain embodiments, the antibody or antibody fragment binding specifically to CD154 comprises a heavy chain constant region, such as an $IgG_1$, $IgG_2$, $IgG_3$, $IgG_4$, IgA, IgE, IgM or IgD constant region. Preferably, the heavy chain constant region is engineered such that it is not glycosylated. Furthermore, the antibody can comprise a light chain constant region, either a kappa light chain constant region or a lambda light chain constant region. Preferably, the antibody comprises a kappa light chain constant region.

The antibody or antibody fragment binding specifically to CD154 of the invention can be incorporated into pharmaceutical compositions suitable for administration to a subject intravenously, subcutaneously or intramuscularly every other week. Typically, the pharmaceutical composition comprises the antibody or antibody fragment binding specifically to CD154 of the invention and/or a pharmaceutically acceptable carrier and/or other active ingredient such as methotrexate or cortisol.

Another embodiment of the invention is a pharmaceutical composition comprising the antibody or antibody fragment binding specifically to CD154 according to any of the embodiments of the invention and a pharmaceutically acceptable carrier wherein the composition is prepared for intravenous, subcutaneous or intramuscular administration to the individual in need thereof. In another embodiment the composition is part of a kit with instructions for use, including instructions and optionally a device for intravenous, subcutaneous or intramuscular administration to the individual in need thereof.

As used herein, "pharmaceutically acceptable carrier" includes any and all solvents, dispersion media, coatings, antibacterial and antifungal agents, isotonic and absorption delaying agents, and the like that are physiologically compatible and are suitable for administration to a subject for the methods described herein. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion. The compositions of this invention may be in a variety of forms. These include, for example, liquid solutions (e.g., injectable and infusible solutions), dispersions or suspensions, powders and liposomes.

The preferred form depends on the intended mode of administration and therapeutic application. Typical preferred compositions are in the form of injectable or infusible solutions, such as compositions similar to those used for passive immunization of humans with other antibodies.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. In certain embodiments, the active compound may be prepared with a carrier that will protect the compound against rapid release, such as a controlled release formulation. [0078] Biodegradable, biocompatible polymers can be used, such as ethylene vinyl acetate, polyethylene glycol (PEG), polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In a further embodiment additional active ingredients are incorporated into the pharmaceutical composition comprising an antibody or antibody fragment binding specifically to CD154 according to the invention. In certain embodiments, an antibody or antibody fragment binding specifically to CD154 is co-formulated with and/or co-administered with one or more additional therapeutic agents. For example, an antibody or antibody fragment binding specifically to CD154 may be co-formulated and/or co-administered with a corticosteroid, a non-steroidal anti-inflammatory drug (NSAID), or therapies targeting the many proinflammatory cytokines known to be involved in the pathogenesis of immune-mediated disorders, such as TNF, IL-1, IL-6, CTLA-4, IFN, or those targeting B-cell activity, such as CD19, CD20 (e.g., rituximab), CD22 (e.g., epratuzumab), BAFF (e.g., belimumab) and BLyS/APRIL (e.g., atacicept), which therapies may or may not themselves be formulated with polyethylene glycol (PEG) moieties.

In a further embodiment, an antibody or antibody fragment binding specifically to CD154 according to the invention, or a composition comprising same, may be used according to the embodiments of the invention in combination with one or more of the foregoing therapeutic agents. Such combination therapies may advantageously utilize lower dosages of the administered therapeutic agents, thus avoiding possible toxicities or complications associated with the various monotherapies.

Autoimmune disease(s) or "inflammatory disease(s) that can be treated with an antibody or antibody fragment binding specifically to CD154 according to the method or use of the invention include but are not limited to systemic lupus erythematosus (SLE), rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemiphigus vulgaris, psoriasis, asthma, allergy, systemic sclerosis, multiple sclerosis, Guillain-Barré syndrome, transverse myelitis, chronic immune polyneuropathy, myasthenia gravis, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, interstitial lung disease.

In addition to the above conditions—for which an autoimmune- or cross-reactive immune-mediated inflammation is established as the primary pathological process—inflammation is also seen as one of a combination of contributory processes in many diseases.

Among these are neurodegenerative disease(s) that can be treated with an antibody or antibody fragment binding specifically to CD154 according to the method or use of the invention are hereditary or sporadic conditions which are characterized by progressive nervous system dysfunction. These disorders are often associated with atrophy of the affected central or peripheral structures of the nervous system. For example, neurodegenerative diseases include but are not limited to Alzheimer's disease, Parkinson's disease, Friedreich's ataxia, Huntington's disease, amyotrophic lateral sclerosis, myasthenia gravis, multifocal motor neuropathy, primary lateral sclerosis, spinal muscular atrophy, Kennedy's disease, and spinocerebellar ataxia.

Similarly, conditions such as atherosclerosis, heart failure, osteoarthritis, non-alcoholic steatohepatitis, irritable bowel syndrome, Crohn's disease, diabetic complications (nephropathy, neuropathy, arteriopathy, retinopathy), asthma, cystic fibrosis, chronic obstructive airway disease, epilepsy, glaucoma, age-related macular degeneration, psychiatric disorders (anxiety, depression, psychosis), chronic fatigue syndrome, enthesiopathies/tendinopathies, prematurity/prenatal infection, obesity/metabolic syndrome, dermatological conditions (acne vulgaris, acne rosacea, solar keratosis), abnormal wound healing (keloid scarring), urogenital disorders (prostatism/prostatitis, overactive bladder syndrome) and cancer development are all amenable to treatment with an antibody or antibody fragment binding specifically to CD154 according to the method or use of the invention.

An antibody or antibody fragment binding specifically to CD154 according to the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397.

To express an antibody or antibody fragment binding specifically to CD154 according to the invention, DNAs encoding the light and heavy chains, obtained by recombinant DNA techniques known in the art, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the genes encoding the heavy and light chain of the antibody or antibody fragment binding specifically to CD154 according to the invention. The expression vector and expression control sequences are chosen to be compatible with the expression host cell used. The light chain gene and the heavy chain gene can be inserted into separate vector or, more typically, both genes are inserted into the same expression vector. The antibody genes are inserted into the expression vector by standard methods (e.g., ligation of complementary restriction sites on the gene fragment and vector, or blunt end ligation if no restriction sites are present). The recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes of an antibody or antibody fragment binding specifically to CD154 according to the invention, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, [e.g., the adenovirus major late promoter (AdMLP)] and polyoma.

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. No. 5,179,017).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the antibody or antibody fragment binding specifically to CD154 according to the invention for use according to the methods of the invention include Chinese Hamster Ovary (CHO cells), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In a preferred system for recombinant expression of the antibody or antibody fragment binding specifically to CD154 according to the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Preferred compositions suitable for administration to a human subject for the methods according to the embodiments of the invention comprise the antibody or antibody fragment binding specifically to CD154 according to the invention and a pharmaceutically acceptable carrier, excipient, or stabilizer. As used herein, "pharmaceutically acceptable carrier" includes any and all solvents, dispersion media, coatings, antibacterial and antifungal agents, isotonic and absorption delaying agents, and the like that are physiologically compatible and are suitable for administration to a subject for the methods described herein. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl-parabens such as methyl- or propyl-paraben; catechol; resorcinol; cyclohexanol; 3-pentanol; and m-cresol); low molecular weight (not more than about 10 amino acid residues) peptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN, PLURONICS or polyethylene glycol.

Therapeutic compositions typically must be sterile and stable under the conditions of manufacture and storage. The composition can be formulated in solution or freeze-dried form.

Comprising in the context of the present specification is intended to meaning including.

Where technically appropriate embodiments of the invention may be combined.

The invention will now be described with reference to the following examples, which are merely illustrative and should not in any way be construed as limiting the scope of the present invention.

EXAMPLES

Example 1

Determination of Binding Affinity.

Biomolecular Interaction Analysis (BIA) was performed using a BIAcore 3000 instrument. Affinipure goat F(ab')$_2$ fragment specific for human IgG, F(ab')$_2$ fragment was immobilised on a CM5 Sensor Chip via amine coupling chemistry to a capture level of approximately 4000 response units (RUs). HBS-EP buffer (10 mM HEPES pH 7.4, 0.15 M NaCl, 3 mM EDTA, 0.005% (v/v)) Surfactant P20) was used as the running buffer with a flow rate of 10 µL/minute (min). A 10 µL injection of test CD154 antibody or Fab at 10 µg/mL was used for capture by the immobilised anti-human IgG-F(ab')$_2$. Human CD154 was titrated over the captured CD154 antibody or Fab at various concentrations (1 nM or below) at a flow rate of 3 µL/min. The surface was regenerated by 2×10 µL injections of 40 mM HCl, followed by a 5 µL injection of 5 mM NaOH at a flow rate of 10 µL/min.

Example 2

Study SL0013: A clinical study of two parts in which, during the first part, ascending single intravenous doses of CDP7657 were assessed for safety, tolerability and pharmacokinetic profiles at 0.004 mg/kg, 0.02 mg/kg, 0.1 mg/kg, 0.5 mg/kg and 1.7 mg/kg in 5 groups, each of 3 healthy male volunteers, followed by a dose of 5 mg/kg in two more groups of 3 healthy male volunteers and 3 healthy female volunteers. Following establishment of acceptable profiles, the second part of the study assessed single intravenous doses at 5 mg/kg, 15 mg/kg, 30 mg/kg and 60 mg/kg in 4 groups of 3 patient volunteers (who had an established diagnosis of systemic lupus erythematosus; SLE). In addition to further assessments of safety, tolerability and pharmacokinetics, the pharmacodynamic effects were also explored using various disease markers.

In performing this study, the basic characteristics of both the anti-CD154 antibody/antibody fragment and its PEG component were established.

Example 3

Study SL0014: A clinical study in which patients with an established diagnosis of SLE were randomised in a double-blind fashion to receive six intravenous doses of CDP7657 (n=16) or matching placebo (n=8) over a period of 10 weeks. The dosing regimen under test (in those receiving active drug) comprised a single loading dose of 30 mg/kg followed by a maintenance dose of 15 mg/kg every 2 weeks thereafter, for a total of 6 doses of CDP7657. In addition to assessing the safety, tolerability and pharmacokinetic profiles of CDP7657 versus placebo, the study explored the immunogenicity (both anti-CD154 and PEG components), effects on various disease markers and effects on clinical disease parameters during and for 18 weeks after treatment. In this way the safety, tolerability and ability of the dosing regimen to deliver disease-modifying effects were established.

---

We claim:

1. A method of treating systemic lupus erythematosus (SLE) comprising:

a) administering an initial loading dose of about 30 mg/kg of a monovalent antibody fragment binding specifically to CD154, the antibody fragment comprising a light chain variable region (LCVR) having a CDR1, a CDR2 and a CDR3 comprising the amino acid sequence of SEQ ID NOs:1, 2 and 3, respectively, and a heavy chain variable region (HCVR) having a CDR1, a CDR2 and a CDR3 comprising the amino acid sequence of SEQ ID NOs: 4, 5 and 6, respectively, to a human subject having SLE; and b) about 2 weeks after the initial loading dose administering a further dose or doses of about 15 mg/kg of the monovalent antibody fragment binding specifically to CD154, with a frequency of about once every other week.

2. The method according to claim 1, wherein the monovalent antibody fragment binding specifically to CD154 is administered to the human subject for at least 12 weeks.

3. The method according to claim 1, wherein said monovalent antibody fragment specifically binding to CD154 contains the VL chain sequence shown in SEQ ID NO:7 and the VH chain sequence shown in SEQ ID NO:8.

4. The method according to claim 3, wherein said monovalent antibody fragment specifically binding to CD154 has the light chain sequence shown in SEQ ID NO:9 and the heavy chain sequences shown in SEQ ID NO:10.

5. The method according to claim 4, wherein said monovalent antibody fragment specifically binding to CD154 is a monovalent Fab' having the light chain sequence shown in SEQ ID NO:9 and the heavy chain sequences shown in SEQ ID NO:10.

6. The method according to claim 5, wherein said monovalent antibody fragment specifically binding to CD154 has
   a) a maleimide group covalently linked to a single thiol group in the modified hinge region; a lysine residue is covalently linked to the maleimide group; and
   b) a methoxypoly(ethyleneglycol) polymer having a molecular weight of approximately 20 KDa is attached to each of the amine groups on the lysine residue.

7. The method according to claim 1, wherein said monovalent antibody fragment specifically binding to CD154 is administered to a subject having SLE and wherein the subject treated achieves an improvement from baseline of one or more of the indices selected from SLEDAI, BILAG and Global Physician assessment.

8. The method according to claim 7, wherein the subject treated achieves a SLEDAI Responder Index 4 (SRI-4).

9. The method according to claim 7, wherein said subject has SLE and wherein the subject treated achieves a 50% improvement from baseline of the SRI-50 index.

10. The method according to claim 7, wherein said subject has SLE and achieves an increase of 20% from baseline or normalization of complement C3 and C4 concentration, or a reduction of 20% of anti-double stranded DNA titre in serum.

11. The method according to claim 7, wherein said subject has SLE and wherein the subject reverts from seropositive to seronegative for anti-double stranded DNA antibodies.

* * * * *

SEQUENCE LISTING

```
<160> NUMBER OF SEQ ID NOS: 10

<210> SEQ ID NO 1
<211> LENGTH: 11
<212> TYPE: PRT
<213> ORGANISM: Artificial Sequence
<220> FEATURE:
<223> OTHER INFORMATION: LC CDR1

<400> SEQUENCE: 1

Arg Ala Ser Glu Asp Leu Tyr Tyr Asn Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: LC CDR2

<400> SEQUENCE: 2

Asp Thr Tyr Arg Leu Ala Asp
1               5

<210> SEQ ID NO 3
<211> LENGTH: 9
<212> TYPE: PRT
```

<213> ORGANISM: Artificial Sequence
<220> FEATURE:
<223> OTHER INFORMATION: LC CDR3

<400> SEQUENCE: 3

Gln Gln Tyr Tyr Lys Phe Pro Phe Thr
1               5

<210> SEQ ID NO 4
<211> LENGTH: 10
<212> TYPE: PRT
<213> ORGANISM: Artificial Sequence
<220> FEATURE:
<223> OTHER INFORMATION: HC CDR1

<400> SEQUENCE: 4

Gly Phe Ser Ser Thr Asn Tyr His Val His
1               5                   10

<210> SEQ ID NO 5
<211> LENGTH: 16
<212> TYPE: PRT
<213> ORGANISM: Artificial Sequence
<220> FEATURE:
<223> OTHER INFORMATION: HC CDR2

<400> SEQUENCE: 5

Val Ile Trp Gly Asp Gly Asp Thr Ser Tyr Asn Ser Val Leu Lys Ser
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: HC CDR3

<400> SEQUENCE: 6

Gln Leu Thr His Tyr Tyr Val Leu Ala Ala
1               5                   10

<210> SEQ ID NO 7
<211> LENGTH: 107
<212> TYPE: PRT
<213> ORGANISM: Artificial Sequence
<220> FEATURE:
<223> OTHER INFORMATION: VLC

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Leu Tyr Tyr Asn
                20                  25                  30

Leu Ala Trp Tyr Gln Arg Lys Pro Gly Lys Ala Pro Lys Leu Leu Ile
            35                  40                  45

Tyr Asp Thr Tyr Arg Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln Gln Tyr Tyr Lys Phe Pro Phe
                85                  90                  95

Thr Phe Gly Gln Gly Thr Lys Val Glu Ile Lys
            100                 105

```
<210> SEQ ID NO 8
<211> LENGTH: 117
<212> TYPE: PRT
<213> ORGANISM: Artificial Sequence
<220> FEATURE:
<223> OTHER INFORMATION: VHC

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
        35                  40                  45

Gly Val Ile Trp Gly Asp Gly Asp Thr Ser Tyr Asn Ser Val Leu Lys
    50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser
        115

<210> SEQ ID NO 9
<211> LENGTH: 214
<212> TYPE: PRT
<213> ORGANISM: Artificial Sequence
<220> FEATURE:
<223> OTHER INFORMATION: LC

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Leu Tyr Tyr Asn
            20                  25                  30

Leu Ala Trp Tyr Gln Arg Lys Pro Gly Lys Ala Pro Lys Leu Leu Ile
        35                  40                  45

Tyr Asp Thr Tyr Arg Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln Gln Tyr Tyr Lys Phe Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 229
<212> TYPE: PRT
<213> ORGANISM: Artificial Sequence
<220> FEATURE:
<223> OTHER INFORMATION: HC Fab'

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Thr Asn Tyr
            20                  25                  30

His Val His Trp Val Arg Gln Ala Pro Gly Lys Gly Leu Glu Trp Met
            35                  40                  45

Gly Val Ile Trp Gly Asp Gly Asp Thr Ser Tyr Asn Ser Val Leu Lys
        50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225
```